(12) United States Patent
Ahn

(10) Patent No.: US 12,241,895 B2
(45) Date of Patent: Mar. 4, 2025

(54) BIO-SENSING DEVICE

(71) Applicant: NDD, INC., Gyeongsangbuk-do (KR)

(72) Inventor: Sae Young Ahn, Seoul (KR)

(73) Assignee: NDD, INC., Gyeongsangbuk-do (KR)

( * ) Notice: Subject to any disclaimer, the term of this patent is extended or adjusted under 35 U.S.C. 154(b) by 975 days.

(21) Appl. No.: 17/283,455

(22) PCT Filed: Oct. 7, 2019

(86) PCT No.: PCT/KR2019/013097
§ 371 (c)(1),
(2) Date: Sep. 13, 2021

(87) PCT Pub. No.: WO2020/076025
PCT Pub. Date: Apr. 16, 2020

(65) Prior Publication Data
US 2021/0396748 A1    Dec. 23, 2021

(30) Foreign Application Priority Data
Oct. 8, 2018   (KR) .................. 10-2018-0119558

(51) Int. Cl.
*G01N 33/543*  (2006.01)
*G01N 27/12*   (2006.01)
*G01N 27/414*  (2006.01)

(52) U.S. Cl.
CPC ....... *G01N 33/54373* (2013.01); *G01N 27/12* (2013.01); *G01N 27/4145* (2013.01)

(58) Field of Classification Search
CPC .... G01N 27/12; G01N 27/4145; G01N 33/49; G01N 33/54373; G01N 33/5438; G01N 33/566
See application file for complete search history.

(56) References Cited

U.S. PATENT DOCUMENTS

| | | | |
|---|---|---|---|
| 6,399,295 B1 * | 6/2002 | Kaylor | G01N 33/54373 436/805 |
| 2004/0082045 A1 * | 4/2004 | Hasegawa | C12Q 1/001 435/174 |
| 2005/0263410 A1 | 12/2005 | Huiung | |
| 2010/0126885 A1 * | 5/2010 | Iechi | G01N 27/4145 257/253 |
| 2018/0059051 A1 * | 3/2018 | Yang | G01N 33/552 |

FOREIGN PATENT DOCUMENTS

| | | | |
|---|---|---|---|
| KR | 1020110116461 | 10/2011 | |
| KR | 1020120085211 | 7/2012 | |
| KR | 1020170112305 | 10/2017 | |
| KR | 1020180048418 | 5/2018 | |
| KR | 1020180057915 | 5/2018 | |
| WO | WO-2018215667 A1 * | 11/2018 | ......... G01N 27/3335 |
| WO | WO-2019145755 A1 * | 8/2019 | ......... G01N 27/4143 |

* cited by examiner

*Primary Examiner* — Jennifer Wecker
(74) *Attorney, Agent, or Firm* — NKL Law; Jae Youn Kim

(57) ABSTRACT

The present invention provides a bio-sensing device comprising: a source electrode and a drain electrode which are arranged to be spaced apart from each other; a sensing film, which is a channel between the source electrode and the drain electrode and has an electrical resistance value that can be changed by a target analyte; and a gate electrode arranged to be spaced apart from the sensing film, wherein the sensing film is formed from a semiconductor including an indium (In) element.

8 Claims, 1 Drawing Sheet

BIO-SENSING DEVICE

TECHNICAL FIELD

The present invention relates to a bio-sensing device, and more particularly, to a bio-sensing device having an electrode structure.

BACKGROUND ART

The test method used for the diagnosis of diseases is mainly based on coloration, fluorescence, etc. by enzyme reaction, but recently, immunoassay using immunity reaction between antigen and antibody has also been used. In the conventional immunoassay, the optical measurement method combining the optical label with the catalytic reaction of the enzyme was the most used. These methods have disadvantages in that they require a complicated procedure that can be performed mainly by a laboratory-oriented and skilled researcher, the apparatus for analysis is large and expensive, and the analysis takes a long time.

DETAILED DESCRIPTION OF THE INVENTION

Technical Problem

The present invention has been made to solve a lot of problems including the above ones, by providing a bio-sensing device that is capable of maximizing the performance of a sensing film and shortening analysis time. However, these problems are for illustrative purposes only, and the scope of the present invention is not limited thereto.

Technical Solution

There is provided a bio-sensing device according to an aspect of the present invention in order to solve the above-described problems. The bio-sensing device includes a source electrode and a drain electrode spaced apart from each other; a sensing film, which is a channel between the source electrode and the drain electrode, and that can vary in electrical resistance by a target analyte; and a gate electrode spaced apart from the sensing film, wherein the sensing film is made of an indium (In)-containing semiconductor.

In the bio-sensing device, the indium (In)-containing semiconductor may include indium tin oxide (ITO), indium gallium zinc oxide (IGZO), zinc indium tin oxide (ZITO), or indium zinc oxide (IZO).

In the bio-sensing device, the indium (In)-containing semiconductor may be an N-type doped semiconductor or a P-type doped semiconductor The bio-sensing device may further include a surface filter membrane disposed on the sensing film and capable of receiving a liquid biological sample containing a target analyte, wherein the surface filter membrane comprises a material that can pass only the target analyte downward.

In the bio-sensing device, the surface filter membrane may include nylon, fibrous or cellulose material.

The bio-sensing device may further include a wall structure supporting the edge of the surface filter membrane to secure a first space capable of accommodating a liquid biological sample that contains a target analyte.

In the bio-sensing device, the surface filter membrane may be disposed on the sensing film to secure a second space disposed between the surface filter membrane and the sensing film and capable of accommodating the target analyte.

In the bio-sensing device, the target analyte may be serum contained in blood and the size of the serum is 1 micrometer or less.

In the bio-sensing device, the target analyte may be at least one selected from the group consisting of body fluids, a protein, a peptide, an aptamer, a nucleic acid, an oligosaccharide, an amino acid, a carbohydrate, a dissolved gas, a sulfur oxide gas, a nitrogen oxide gas, a residual pesticide, a heavy metal and an environmentally harmful substance.

The bio-sensing device may further include a receptor attached on the sensing film and capable of binding to a target analyte.

In the bio-sensing device, the receptor may be attached to the sensing film by a functional group and may be any one or more selected from the group consisting of an enzyme substrate, a ligand, an amino acid, a peptide, an aptamer, a protein, a nucleic acid, a lipid and a carbohydrate.

In the bio-sensing device, the functional group may be at least one selected from the group consisting of an amine group, a carboxyl group and a thiol group.

Advantageous Effects

According to the embodiments of the present invention as described above, it is possible to provide a bio-sensing device that is capable of maximizing the performance of a sensing film and shortening analysis time. Of course, the scope of the present invention is not limited by these effects.

MODE OF THE INVENTION

Figure 1:
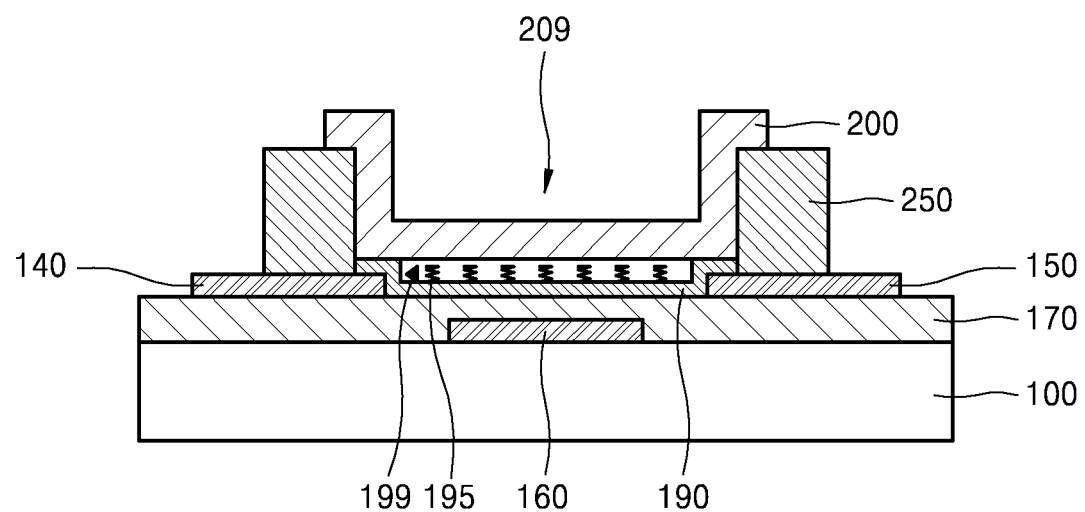
FIG. 1 is a schematic view illustrating a bio-sensing device according to an embodiment of the present invention.

Hereinafter, embodiments of the present invention will be described in detail with reference to the accompanying drawings. In the specification, it will be understood that when an element, such as a layer, region, or substrate, is referred to as being "on," "connected to," "stacked on" or "coupled to" another element, it can be directly "on," "connected to," "stacked on" or "coupled to" the other element or intervening elements may be present. In contrast, when an element is referred to as being "directly on," "directly connected to" or "directly coupled to" another element, there are no intervening elements present.

In the drawings, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Furthermore, the thickness and size of each layer in the drawings may be exaggerated for convenience and clarity of explanation. Like numerals refer to like elements.

FIG. 1 is a schematic view illustrating a bio-sensing device according to an embodiment of the present invention.

Figure 2:
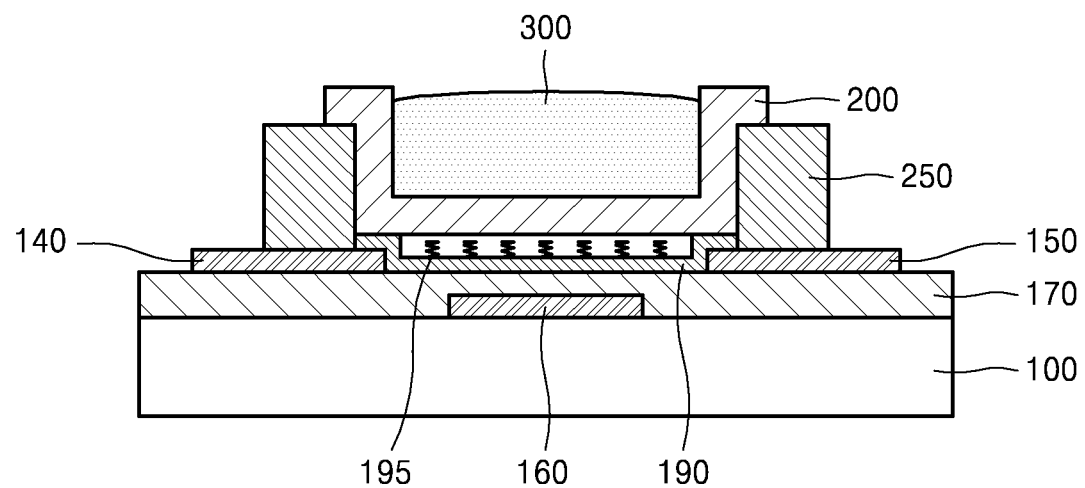
FIG. 2 is a schematic view illustrating a state in which a liquid biological sample is received in a bio-sensing device according to an embodiment of the present invention.

FIG. 2 is a schematic view illustrating a state in which a liquid biological sample is received in a bio-sensing device according to an embodiment of the present invention.

Referring to FIGS. 1 and 2, a bio-sensing device according to an embodiment of the present invention includes a source electrode 140 and a drain electrode 150 spaced apart from each other on a substrate 100, a sensing film 190 that forms a channel between the source electrode and the drain electrode, and a gate electrode 160 spaced apart from the sensing film.

The substrate 100 may include, for example, a glass substrate or a silicon substrate, etc. In the case of a silicon substrate, an insulating layer (not shown) may be further interposed between the gate electrode 160 and the substrate 100.

The gate electrode 160 is disposed to be spaced apart from the source electrode 140 and the drain electrode 150. In addition, the insulating member 170 is interposed between the sensing film 190 and the gate electrode 160, and may be interposed between the source electrode 140 and the gate electrode 160 and between the drain electrode 150 and the gate electrode 160. The thickness, shape, and position structure of the gate electrode 160 and the insulating member 170 shown in the drawings are schematically illustrated, and may be embodied in various embodiments, and the technical idea of the present invention is not limited by the detailed position structure and shape of the gate electrode 160.

One end of the sensing film 190 is connected to the source electrode 140 and the other end of the sensing film 190 is connected to the drain electrode 150. The sensing film 190 is made of an indium (In)-containing semiconductor. The indium (In)-containing semiconductor, which constitutes the sensing film 190, may include, for example, indium tin oxide (ITO), indium gallium zinc oxide (IGZO), zinc indium tin oxide (ZITO), or indium zinc oxide (IZO). However, the 'indium (In)-containing semiconductor' disclosed in the present embodiment is not limited to the above illustrative materials, and may include any materials that include indium and have semiconductor properties.

Meanwhile, the indium (In)-containing semiconductor may be an N-type doped semiconductor or a P-type doped semiconductor.

The sensing film 190 may vary in electrical resistance by a target analyte.

As an example of an indium (In)-containing semiconductor, an ITO film is a material film in which tin (Sn) is added, in the form of an oxide ($SnO_2$), to indium oxide ($In_2O_3$), and tin (Sn) acts as a substitutional solid solution and enters the location of indium (In) so that free electrons are generated. The ITO is a semiconductor with a large energy band gap of 3.75 eV to 4.55 eV, has a high light transmittance in the visible light region, and has a high carrier concentration of $10^{20}$ $cm^{-3}$ to $10^{21}$ $cm^{-3}$ and a relatively low resistivity of $10^{-4}$ $\Omega\cdot cm$. According to the calculation of the electron band structure, the structure of the undoped indium oxide ($In_2O_3$) has the ground state of a single free electron conduction band with s orbital electron characteristics and shows semiconductor properties because the 5 s orbital state of In and the 2 s orbital state of O are mixed.

The bio-sensing device may further include a surface filter membrane 200 disposed on the sensing film 190 and capable of receiving a liquid biological sample 300 containing a target analyte. The surface filter membrane 200 may be made of a material that can pass only the target analyte downward. For example, the surface filter membrane 200 may comprise nylon, fibrous, or cellulose material.

The bio-sensing device includes a wall structure 250 supporting the edge of the surface filter membrane 200 to secure a first space 209 capable of accommodating a liquid biological sample 300 containing a target analyte. Meanwhile, the surface filter membrane 200 may be disposed on the sensing film 190 to secure a second space 199 between the surface filter membrane 200 and the sensing film 190, capable of accommodating the target analyte that has passed through the surface filter membrane 200.

In order to implement the above-described structure, the wall structure 250 has a shape protruding upward from the source electrode 140 and the drain electrode 150, one end of the sensing film 190 is in contact with the wall structure 250 protruding from the source electrode 140, the other end of the sensing film 190 is in contact with the wall structure 250 protruding from the drain electrode 150, and one end and the other end of the surface filter membrane 200 may respectively have a shape of spanning the wall structure 250 protruding from the source electrode 140 and the drain electrode 150.

The receptor 195 may be attached to the sensing film 190 by a functional group. For example, the receptor 195 may be any one or more selected from the group consisting of an enzyme substrate, a ligand, an amino acid, a peptide, an aptamer, a protein, a nucleic acid, a lipid and a carbohydrate. Meanwhile, the functional group may be at least one selected from the group consisting of, for example, an amine group, a carboxyl group and a thiol group.

The target analyte may be at least one selected from the group consisting of, for example, body fluids, a protein, an aptamer, a peptide, a nucleic acid, an oligosaccharide, an amino acid, a carbohydrate, a dissolved gas, a sulfur oxide gas, a nitrogen oxide gas, a residual pesticide, a heavy metal and an environmentally harmful substance.

For a specific example, the liquid biological sample 300 may be human blood, and the target analyte may be serum contained in the blood. Typically, blood consists of white blood cells, red blood cells, plasma, serum, etc. Among them, white blood cells have a particle size of about 10 micrometers, red blood cells have a particle size of about 7 micrometers, and plasma has a particle size of about 8 micrometers, whereas serum may have a particle size of 1 micrometer or less. The surface filter membrane 200 is made of a material through which serum of 1 micrometer or less can pass from the blood contained in the first space 209 to the second space 199. For example, the surface filter membrane 200 may comprise nylon, fibrous, or cellulose material.

Meanwhile, in the bio-sensing device according to a modified embodiment of the present invention, the sensing film 190 may be made of a material that can vary in resistance by reacting directly with the target analyte without interposing the receptor 195.

The bio-sensing device according to an embodiment of the present invention can be used as an inspection device that is used for disease diagnosis and can be used as a sensing device that uses an immune reaction between an antigen and an antibody depending on the kind of a sensing film and a receptor. In this case, it is advantageous that, since the result of electrical measurement is utilized, a complicated procedure is not required in the analysis process, the apparatus for analysis is relatively inexpensive, and the analysis does not take a long time.

Meanwhile, since the structure shown in FIG. 1 can be understood as a unit cell of a bio-sensing device, if the size of the unit cell per substrate 100 is further reduced to a nano size, the number of unit cells can be increased to hundreds of thousands to millions. Thus, by increasing the number of unit cells per substrate, the bio-sensing device of the present invention is capable of diagnosing various diseases and drastically reducing the inspection cost due to the shortened inspection time.

While the present invention has been particularly shown and described with reference to embodiments shown in the drawings, it is only for illustrative purposes. It will be understood by those skilled in the art that various modifications and equivalent embodiments may be made. Therefore, the scope of the present invention should be determined by the technical idea of the appended claims.

The invention claimed is:

1. A bio-sensing device comprising:
a source electrode and a drain electrode spaced apart from each other on a lower substrate;
a sensing film, which is a channel between the source electrode and the drain electrode, and wherein the sensing film is configured to vary in electrical resistance by a target analyte; a gate electrode spaced apart from the sensing film;
a surface filter membrane disposed on the sensing film and configured to receive a liquid biological sample containing the target analyte; and
a wall structure supporting an edge of the surface filter membrane to secure a first space configured to accommodate the liquid biological sample that contains the target analyte, wherein the sensing film is made of an indium (In)-containing semiconductor, wherein the surface filter membrane comprises a material that is configured to pass only the target analyte downward, wherein the surface filter membrane is disposed on the sensing film to secure a second space between the surface filter membrane and the sensing film, the second space being configured to accommodate the target analyte, and wherein the first space and the second space are separated and stacked while being spaced apart vertically on the lower substrate.

2. The bio-sensing device of claim 1, wherein the indium (In)-containing semiconductor includes indium tin oxide (ITO), indium gallium zinc oxide (IGZO), zinc indium tin oxide (ZITO), or indium zinc oxide (IZO).

3. The bio-sensing device of claim 1, wherein the surface filter membrane comprises nylon, fibrous or cellulose material.

4. The bio-sensing device of claim 1, wherein the target analyte is serum contained in blood and the size of the serum is 1 micrometer or less.

5. The bio-sensing device of claim 1, wherein the target analyte is at least one selected from the group consisting of body fluids, a protein, a peptide, an aptamer, a nucleic acid, an oligosaccharide, an amino acid, a carbohydrate, a dissolved gas, a sulfur oxide gas, a nitrogen oxide gas, a residual pesticide, a heavy metal and an environmentally harmful substance.

6. The bio-sensing device of claim 1, further comprising:
a receptor attached on the sensing film and capable of binding to a target analyte.

7. The bio-sensing device of claim 6, wherein the receptor is attached to the sensing film by a functional group, and is any one or more selected from the group consisting of an enzyme substrate, a ligand, an amino acid, a peptide, an aptamer, a protein, a nucleic acid, a lipid and a carbohydrate.

8. The bio-sensing device of claim 7, wherein the functional group is at least one selected from the group consisting of an amine group, a carboxyl group and a thiol group.

* * * * *